US006500455B1

(12) United States Patent
Frantsits

(10) Patent No.: US 6,500,455 B1
(45) Date of Patent: Dec. 31, 2002

(54) TOLPERISON-CONTAINING, PHARMACEUTICAL PREPARATION FOR ORAL ADMINISTRATION

(75) Inventor: Werner Frantsits, Vienna (AT)

(73) Assignee: Sanochemia Pharmazeutika, Vienna (AT)

( * ) Notice: Subject to any disclaimer, the term of this patent is extended or adjusted under 35 U.S.C. 154(b) by 0 days.

(21) Appl. No.: 09/937,710

(22) PCT Filed: Nov. 16, 1999

(86) PCT No.: PCT/AT99/00276

§ 371 (c)(1),
(2), (4) Date: Oct. 1, 2001

(87) PCT Pub. No.: WO00/59508

PCT Pub. Date: Oct. 12, 2000

(30) Foreign Application Priority Data

Apr. 1, 1999 (AT) ................................................ 594/99

(51) Int. Cl.[7] .............................. A61K 9/20; A61K 9/22; A61K 9/16; A61K 9/48; B05D 7/00
(52) U.S. Cl. ........................ 424/463; 424/464; 424/465; 424/468; 424/489; 424/470; 424/472; 424/451; 424/463; 424/494; 424/495; 427/213.3; 427/213.31
(58) Field of Search .................. 424/463, 464, 424/465, 468, 489, 470, 472, 451, 494, 495; 427/213

(56) References Cited

U.S. PATENT DOCUMENTS 4,702,918 A  * 10/1987  Ushimaru et al.
4,996,058 A       2/1991  Sinnreich
5,128,145 A  *  7/1992  Edgren et al.
5,651,990 A  *  7/1997  Takada et al.
5,731,006 A  *  3/1998  Akiyama et al.
5,811,547 A  *  9/1998  Nakamichi et al.

FOREIGN PATENT DOCUMENTS

| EP | 0 273 375 A2 | 7/1988 |
| EP | 0 295 411 B1 | 9/1990 |
| EP | 0 454 089 A1 * | 10/1991 |
| GB | 1 480 175 | 7/1977 |
| JP | 51091315 A | 8/1976 |
| JP | 53040779 | 4/1978 |
| JP | 58135806 | 8/1983 |

OTHER PUBLICATIONS

Yokoyama, T.; Fukuda, K.; Mori, S.; Ogawa, M.; Nagasawa, K.; "Determination of tolperisone enantiomers in plasma and their disposition in rats", Chem Pharm Bull (Tokyo), Jan. 1992;40(1): pp. 272–274.*

* cited by examiner

Primary Examiner—Thurman K. Page
Assistant Examiner—Simon J. Oh
(74) Attorney, Agent, or Firm—Young & Thompson

(57) ABSTRACT

A pharmaceutical preparation containing Tolperison or a salt thereof as an active ingredient in the form of a racemic mixture which can be a 50/50/-racemat or a racemat with the perponderant content of the (−) -isomer of Tolperison. The pharmaceutical preparation is formulated as a solid or liquid medicament for oral administration. The active ingredient Tolperison that is present as 50/50-racemat or as racemat with a preponderant content of the (−)-isomer or the (+)-isomer is liberated from the preparation in the human body in a delayed manner and preferably in the intestinal canal.

22 Claims, No Drawings

TOLPERISON-CONTAINING, PHARMACEUTICAL PREPARATION FOR ORAL ADMINISTRATION

This application is a 37 of PCT/AT 99/00276 filed Nov. 16, 1999.

The invention relates to a pharmaceutical preparation for oral administration which contains Tolperison or a salt thereof.

Tolperison-containing drugs are known in various preparation forms. Thus EP 0 295 411 B describes a pharmaceutical preparation for percutaneous administration of Tolperison or a salt thereof.

Other forms of administration of Tolperison-containing drugs are also known. Thus JP 51091315 A describes a stable syrup of Tolperison which is intended for oral administrations.

Tolperison is the international generic name for the muscle relaxant (RS)-2,4'-dimethyl-3-piperidonopropriophenone) with the empirical formula $C_{16}H_{23}NO$.

Tolperison and its salts are known as an agent for improving not only different symptoms with respect to spastic paralysis, but also muscle tone which originates from diseases such as cervical syndrome, inflammation of the joints and back pain.

The disadvantage in oral administration of Tolperison or a salt thereof is that the action quickly diminishes so that Tolperison-containing preparations must be taken several times daily and that the gastrointestinal tract of the patient can be damaged.

The disadvantage of percutaneous use, as is known from EP 0 295 411 B, is the only inadequate percutaneous absorption of the pharmaceutical active ingredient, Tolperison.

The active ingredient Tolperison is present as a 50/50 racemate. Studies have shown that up to 90% of the (−) isomer and up to only 10% of the (+) isomer of Tolperison are present in the blood. For a long time it had not been conclusively clarified whether the 90/10 racemate present in the blood (of humans) is formed by re-racemization or by intensified resorption of the (−) isomer.

The object of the invention is to make available a preparation which contains Tolperison or a salt thereof which can be orally administered without the disadvantages of the known orally administered preparations of Tolperison occurring.

This object is achieved as claimed in the invention with a preparation which is characterized in claim 1.

Preferred and advantageous embodiments of the preparation as claimed in the invention are the subject matter of the dependent claims.

The preparation as claimed in the invention replaces the action which rapidly fades in the known oral preparations of Tolperison or its salts by a long lasting action since the preparation is produced such that the active ingredient Tolperison or the salt thereof is released only on a delayed basis. In particular, in the preparation as claimed in the invention it can be advantageous that the delay of the release of the active ingredient Tolperison is set such that the Tolperison is resorbed predominantly in the intestine.

The advantages of controlled release of pharmaceutical active ingredients are well known in the area of pharmaceuticals and consist among others in that the desired content of the active ingredient in the blood can be maintained over a comparatively long time interval so that the patient is no longer compelled to take a drug several times daily.

The preparations as claimed in the invention with delayed release of Tolperison or salts thereof can be present for example in combination with various hydrogels which can be of synthetic, semisynthetic or natural origin.

Oral preparations with delayed release of the active ingredient—here Tolperison or a salt thereof—should be adjustable such that the release rates and profiles can be set according to the physiological and chronotherapeutic requirements. This is allowed by the preparation as claimed in the invention. Studies have shown that the (−) isomer and the (+) isomer of Tolperison are almost identically effective. Therefore racemic mixtures of the isomers of Tolperison are also essentially identically active as one or the other isomer alone.

Tolperison can be present in the preparations as claimed in the invention as a 50/50 racemate or as a racemic mixture which differs from the 50/50 racemate. Racemates in which the content of the (−) isomer is higher than that of the (+) isomer are likewise used. Racemates with a predominant proportion of the (−) isomer of Tolperison (2,4'-dimethyl-3-piperidonopropriophenone) can be present as 90/10 racemates.

Examples of pharmaceutical preparations as claimed in this invention are given below.

EXAMPLE 1

Crystalline Tolperison hydrochloride (50/50 racemate) with a grain size of 30 and 60 mesh was placed in a coating column operated with an air flow and was coated with a mixture of a polymer solution in chloroform which contains ethyl cellulose, hydroxypropyl cellulose and methanol. The coating solution was sprayed with 2.5 bar pressure into the column with a speed of 60 ml/min. The inlet temperature was roughly 60° C. After feed of the coating was ended, the Tolperison crystals which were dried quickly and which were coated with the polymer were removed from the coating column to the bottom.

EXAMPLE 2

In this example an aqueous liquid suspension of Tolperison (50/50 racemate) with delayed release was produced. The aqueous vehicle was saturated with Tolperison and contained microencapsulated Tolperison suspended in water. Tolperison is contained in the saturated aqueous solution in an amount which corresponds to its solubility. By administering a suspension of Tolperison-containing microcapsules in a Tolperison-saturated aqueous vehicle it is possible to make available Tolperison in a sufficient dose. This can be done by the Tolperison being made available in the form of suspended, Tolperison-containing microcapsules and Tolperison as an aqueous solution in the mixing ratio which is required at the time. The amount of Tolperison in the microcapsules can be increased in order to take into account the amount of Tolperison solution replaced in the microcapsules.

EXAMPLE 3

In this example, first a binder for the delayed release of the active ingredient Tolperison is produced and then the active ingredient Tolperison (50/50 racemate) is added to it, whereupon it is ultimately pressed into tablets. The binder for delayed release of Tolperison is produced by dry-mixing the corresponding amounts of xanthene gum, carob gum, calcium sulfate and dextrose in a high speed mixer/granulator for 2 minutes. During mixing, water was added to the initially still dry mixture and then granulation was continued for 2 minutes. The granules obtained were dried in a fluid-bed drier. The dried granules obtained in this way were then ground to a grain size of 20 mesh. For example the binder was produced from a mixture of 25% xanthene gum, 25% carob gum, 40% cellulose, 10% calcium sulfate and 10% water (added during granulation).

Next the binder for delayed release was mixed with the amount of Tolperison which was used as the hydrochloride salt desired at the time in a high speed mixer/granulator for 2 minutes. With the mixer running a solution of ethyl cellulose in ethanol was added to the mixture and the mixture was granulated for 2 minutes. The resulting granules were dried in a fluid-bed drier and then ground to a grain size of 20 mesh. After adding a suitable tabletting aid (for example, sodium stearyl fumarate) mixing was continued for another 5 minutes. The mixture ultimately obtained was pressed into tablets.

The tablets produced in this way can be influenced in their release rate by the amount of gum in the preparations being increased, since then the release of the active ingredient (Tolperison) decreases. Thus, it is possible for example to make available a 24 hour dose of Tolperison with tablets according to example 3.

EXAMPLE 4

The tablet which contains Tolperison hydrochloride (50/50 racemate) as the active ingredient with delayed release of the active ingredient contains Tolperison hydrochloride Lactose Methyl hydroxypropyl cellulose Dye Water for granulate formation Magnesium stearate Finely dispersed silicon dioxide.

The procedure for producing the tablets was as follows:

The dye was stirred into water, the Tolperison hydrochloride, lactose and methyl hydroxypropyl cellulose were added to the fluidized-bed granulator and granulated with the aqueous solution which contains the dye. The granules obtained were worked together with magnesium stearate and finely dispersed silicon dioxide through a screen with a mesh width of 1.25 mm and homogenized in a mixer. The mixture obtained in this way was pressed into tablets on a tabletting machine.

EXAMPLE 5

According to the specification from example 1 a preparation which contains a 90/10 racemate (with a predominant proportion of the (−) isomer) of Tolperison was produced.

EXAMPLE 6

According to the specification from example 2 a preparation which contains a 80/20 racemate (with a predominant proportion of the (−) isomer) of Tolperison was produced.

EXAMPLE 7

According to the specification from example 2 a preparation which contains a 70/30 racemate (with a predominant proportion of the (−) isomer) of Tolperison was produced.

EXAMPLE 8

According to the specification from example 3 a preparation which contains a 90/10 racemate (with a predominant proportion of the (−) isomer) of Tolperison was produced.

EXAMPLE 9

According to the specification from example 4 a preparation which contains a 65/35 racemate (with a predominant proportion of the (−) isomer) of Tolperison was produced.

EXAMPLE 10

According to the specification from example 4 a preparation which contains a 90/10 racemate (with a predominant proportion of the (−) isomer) of Tolperison was produced.

In summary, one embodiment of the invention can be described as follows.

A pharmaceutical preparation contains Tolperison or a salt thereof as the active ingredient in the form of a racemic mixture which can be a 50/50 racemate or racemate with a predominant proportion of the (−) isomer of Tolperison. The pharmaceutical preparation which is intended for oral administration is formulated as a solid or liquid, orally administered drug, the active ingredient, Tolperison, which is present as 50/50 racemate or as a racemate with a predominant proportion of the (−) or (+) isomer, being released from the preparation in the human body, preferably in the intestinal tract.

What is claimed is:

1. Process for producing a pharmaceutical preparation for oral administration which contains tolperisone or a salt thereof, the preparation being prepared for delayed release of the active ingredient tolperisone, characterized in that the crystalline, racemic tolperisone is coated in a coating column which is operated with an air flow with a mixture of methanol and a solution of synthetic, semisynthetic or natural hydrogels in chloroform.

2. Process as claimed in claim 1, wherein ethyl cellulose and hydroxypropyl cellulose are used as the hydrogels.

3. Process as claimed in claim 1 wherein the solution is sprayed into the coating column with 2.5 bar pressure with a speed of 60 ml/min.

4. Process as claimed in claim 1, wherein the coating solution is sprayed into the coating column with a temperature of roughly 60° C. at the inlet.

5. Process as claimed in claim 1, wherein the crystalline tolperisone hydrochloride is coated as a 50/50 racemate.

6. Process as claimed in claim 1, wherein crystalline tolperisone hydrochloride is coated as a 90/10 racemate with a predominant proportion of (−) isomers.

7. Process for producing a pharmaceutical preparation for oral administration which contains tolperisone or a salt thereof, the preparation being prepared for delayed release of the active ingredient tolperisone, characterized in that microcapsules which contain tolperisone are suspended in an aqueous solution of tolperisone which is saturated with tolperisone.

8. Process as claimed in claim 7, wherein the dissolved tolperisone and the tolperisone which is contained in the microcapsules are present as a 50/50 racemate.

9. Process as claimed in claim 7, wherein the dissolved tolperisone and the tolperisone which is contained in the microcapsules are present as a 80/20 racemate with a predominant proportion of (−) isomers.

10. Process as claimed in claim 7, wherein the dissolved tolperisone and the tolperisone which is contained in the microcapsules are present as a 70/30 racemate with a predominant proportion of (−) isomers.

11. Process for producing a pharmaceutical preparation for oral administration which contains tolperisone or a salt thereof, the preparation being prepared for delayed release of the active ingredient tolperisone, characterized in that a binder is produced by granulating a synthetic, semisynthetic or natural hydrogel after adding water, wherein the granules obtained in this way are dried, wherein the grainy binder obtained in this way is mixed with tolperisone, diluted while mixing with a solution of a synthetic, semisynthetic or natural hydrogel in ethanol and then is granulated and wherein the granules obtained in this way are mixed with a tabletting aid and pressed into tablets.

12. Process as claimed in claim 11, wherein xanthan gum, carob gum, calcium sulfate are granulated after adding water.

13. Process as claimed in claim 11, wherein the hydrogel is mixed dry with dextrose and the mixture obtained in this way is granulated after adding water.

14. Process as claimed in claim 11, wherein the grainy binder and tolperisone are diluted while mixing with a solution of ethyl cellulose in ethanol.

15. Process as claimed in claim 11, wherein the binder is produced by mixing 25% xanthan gum, 25% carob gum, 40% cellulose, 10% calcium sulfate and 10% water which is added during granulation.

16. Process as claimed in claim 1, wherein sodium stearyl fumarate is used as the tabletting aid.

17. Process as claimed in claim 11, wherein the tolperisone is used as a 90/10 racemate with a predominant proportion of the (−) isomers.

18. Process for producing a pharmaceutical preparation for oral administration which contains tolperisone or a salt thereof, the preparation being prepared for delayed release of the active ingredient tolperisone, wherein tolperisone, lactose, and a synthetic, semisynthetic or natural hydrogel are granulated in a granulator with the addition of an aqueous solution which contains a dye, wherein the granules obtained in this way together with magnesium stearate and finely dispersed silicon dioxide are worked through a screen and homogenized in a mixer and wherein the mixture which was obtained in this way is pressed into tablets.

19. Process as claimed in claim 18, wherein methyl hydroxypropyl cellulose is used as the hydrogel.

20. Process as claimed in claim 18, wherein the granules together with magnesium stearate and finely dispersed silicon dioxide are worked through a screen with a mesh width of 1.25 mm.

21. Process as claimed in claim 18, wherein the tolperisone is used as a 65/35 racemate with a predominant proportion of the (−) isomers.

22. Process as claimed in claim 18, wherein the tolperisone is used as a 90/10 racemate with a predominant proportion of the (−) isomers.

* * * * *